United States Patent
Pittaluga et al.

(10) Patent No.: US 11,812,994 B2
(45) Date of Patent: Nov. 14, 2023

(54) DEVICE AND METHOD FOR THE TREATMENT OF TELANGIECTASIAS

(71) Applicants: Paul Pittaluga, Cagnes-sur-mer (FR); Sylvain Chastanet, Nice (FR)

(72) Inventors: Paul Pittaluga, Cagnes-sur-mer (FR); Sylvain Chastanet, Nice (FR)

( * ) Notice: Subject to any disclaimer, the term of this patent is extended or adjusted under 35 U.S.C. 154(b) by 551 days.

(21) Appl. No.: 16/848,147

(22) Filed: Apr. 14, 2020

(65) Prior Publication Data

US 2020/0323560 A1  Oct. 15, 2020

(30) Foreign Application Priority Data

Apr. 15, 2019 (FR) ...................................... 1904017

(51) Int. Cl.
| | | |
|---|---|---|
| *A61B 17/34* | (2006.01) | |
| *A61B 17/32* | (2006.01) | |
| *A61B 17/00* | (2006.01) | |
| *A61B 17/3211* | (2006.01) | |

(52) U.S. Cl.
CPC .......... *A61B 17/3494* (2013.01); *A61B 17/32* (2013.01); *A61B 17/3401* (2013.01); *A61B 2017/00336* (2013.01); *A61B 2017/320077* (2017.08); *A61B 2017/32113* (2013.01)

(58) Field of Classification Search
CPC ..... A61B 17/20; A61B 17/3209; A61B 17/34; A61B 17/3401; A61B 17/3417; A61B 17/3478; A61B 17/3494; A61B 2017/00336; A61B 2017/320075; A61B 2017/320077; A61B 2017/32093; A61B 2017/32113; A61B 5/14514; A61B 5/150022; A61B 5/150282; A61B 5/150984; A61B 5/150992; A61B 5/151; A61B 5/15103; A61B 5/15146; A61B 5/15186; A61B 5/153; A61B 5/154; A61B 2018/00452; A61B 2018/00458; A61B 2090/036; A61M 37/0015; A61M 2037/0023

See application file for complete search history.

(56) References Cited

U.S. PATENT DOCUMENTS

| | | | |
|---|---|---|---|
| 2,893,392 A | | 7/1959 | Wagner et al. |
| 5,749,886 A | * | 5/1998 | Abidin ............... A61B 17/3211 30/162 |
| 2002/0029060 A1 | * | 3/2002 | Hogendijk ..... A61B 17/320016 606/185 |

(Continued)

FOREIGN PATENT DOCUMENTS

WO    2012144718 A1    10/2012

OTHER PUBLICATIONS

French Search Report and Written Opinion dated Jan. 7, 2020 in priority application No. FR1904017; w/ English machine translation (total 20 pages).

*Primary Examiner* — Robert A Lynch
(74) *Attorney, Agent, or Firm* — Seckel IP, PLLC (57) ABSTRACT

A device for destroying the blood vessels forming telangiectasias includes: a single blade; and a device body, the body having firstly a gripping part and secondly a support for the blade; and a stop situated at a distance of between 0.1 and 1 cm from a distal end of the blade limiting the penetration of the blade, in the thickness of the skin, to a depth of less than 1 cm.

20 Claims, 4 Drawing Sheets

(56) References Cited

U.S. PATENT DOCUMENTS

| | | | |
|---|---|---|---|
| 2007/0269393 A1* | 11/2007 | Wepfer | A61P 23/02 |
| | | | 514/35 |
| 2009/0048537 A1* | 2/2009 | Lydon | A61L 29/041 |
| | | | 606/167 |
| 2011/0118759 A1* | 5/2011 | Teichman | A61B 17/3417 |
| | | | 606/151 |
| 2011/0251602 A1 | 10/2011 | Anderson et al. | |
| 2013/0197558 A1* | 8/2013 | Ingold, Jr. | A61B 17/32093 |
| | | | 606/185 |
| 2016/0262793 A1* | 9/2016 | Heinen | A61B 17/3417 |

* cited by examiner

DEVICE AND METHOD FOR THE TREATMENT OF TELANGIECTASIAS

TECHNICAL FIELD OF THE INVENTION

The present invention relates to a device for destroying the blood vessels forming telangiectasias. The invention also relates to a method for treating telangiectasias as well as a kit for treating telangiectasias.

PRIOR ART

The skin is mainly composed of three superimposed tissues: the epidermis, the dermis and the hypodermis. The epidermis, the surface layer in contact with the external environment, has a variable thickness, ranging from approximately 0.05 mm at the eyelid to 1.5 mm at the palms and the soles of the feet. It is formed by a layered, keratinised, pavement, squamous and non-vascularised epithelial tissue that covers the dermis The dermis, the intermediate layer between the epidermis and the hypodermis, is a vascularised connective tissue. It has a mean thickness of 1 to 2 mm: from 3 to 4 mm at the palm of the hands and the soles of the feet and approximately 0.6 mm at the eyelids. The hypodermis is the deepest layer of the skin and is formed by a richly vascularised loose connective tissue that, depending on the area of the body, contains adipose tissue to a greater or lesser extent. The thickness thereof is variable.

Telangiectasias are permanent dilations of the intradermal blood vessels. Telangiectasias concern small visible superficial blood vessels, red, violet or blue, which may be situated on the face, the top of the chest, the neck, the lower limbs or other parts of the body. The blood vessels forming the telangiectasias, which may include swollen blood vessels, varicosities or red, violet or blue skin spots, are not necessary to any essential bodily function. They may be composed of abnormal aggregates of arterioles, capillaries and/or veinlets. They correspond to vascular lesions, the outline of which is thin and tortuous, measuring from a few millimetres to a few centimetres in length, often in a tree or lattice form. They are to be differentiated from varicose veins in that they have no repercussion on health and do not relate to the same type of blood vessel.

The conventional method for treating telangiectasias is sclerotherapy. According to this method, a sclerosing agent is injected by means of a very small needle and causes fibrosis of the vein, which then gradually disappears. This method, used for treating the very great majority of telangiectasias, suffers from irregular and inconsistent results. In addition, use thereof in the area of the foot and/or of the ankle is not recommended because of the risk of skin lesion, thrombosis or associated ischaemia.

Other treatment methods exist, such as transcutaneous laser or the application of radio frequencies. These methods however also suffer from irregular and inconsistent results, in addition to having recourse to often expensive equipment.

A need exists for a simple and innovative device for the aesthetic treatment of telangiectasias offering regular and effective results, whatever the part of the body concerned.

SUMMARY OF THE INVENTION

Having regard to the above, one technical problem that the invention sets out to solve is treating telangiectasias in a regular, effective and simple manner, whatever the part of the body on which the telangiectasia is situated, applied to treat solely telangiectasias, without degradation to veinlets, veins or other small blood vessels that do not form the telangiectasias.

The first object of the solution of the invention to this technical problem is a device for destroying the blood vessels forming the telangiectasias comprising: a single blade; and a device body, said body comprising, firstly, a means for gripping said device, and secondly a support for said one blade, said blade comprising two lateral edges and forms, at the distal end thereof, a point, at least one of said two lateral edges being sharp, and in that said device comprises a stop situated at a distance of between 0.1 and 0.6 cm from the distal end of said one blade limiting the penetration of the blade, in the thickness of the skin, to a depth of less than or equal to 0.6 cm.

Thus the device of the invention makes it possible to destroy, in a mechanical and simple manner, the blood vessels forming the telangiectasias without penetrating the dermis too deeply, by virtue of the stop.

Advantageously,—the stop limits the penetration of the blade, in the thickness of the skin, to a depth of less than 0.6 cm;—the stop is situated at a distance of between 0.2 and 0.4 cm from the distal end of said blade;—said gripping means is in the form of a handpiece; and—said device body is hollow, said blade is retractable into said device body and said device body further comprises a needle, said needle being inside the device body when said blade is outside, and vice versa.

The second object of the invention is a method for the aesthetic treatment of telangiectasias, comprising local anaesthesia; exsanguination of the blood vessels forming the telangiectasias; and mechanical destruction of the blood vessels forming the telangiectasias by means of the aforementioned device.

Thus the method of the invention makes it possible to reduce ecchymoses and haematomas compared with the methods of the prior art, and affords lasting destruction of the telangiectasias, preventing recanalisation, by virtue of the exsanguination. The absence of the injection of a sclerosing agent or the use of a source of heat also allows use thereof on all parts of the body.

Advantageously,—the local anaesthesia and the exsanguination the blood vessels forming the telangiectasias are implemented simultaneously by an infiltration, in particular by the injection of an anaesthetic;—the local anaesthesia is implemented by the application of an anaesthetic cream;—the local anaesthesia is implemented by the application of an anaesthetic cream and the exsanguination is implemented by an injection of liquid, preferably an injection of water; and—the mechanical destruction of the blood vessels forming the telangiectasias is implemented over the length of the blood vessel, by incisions of the blood vessel, preferably spaced apart by 0.1 to 0.5 cm.

A third object of the invention is a device for destroying the blood vessels forming the telangiectasias as described above for implementing the method of the invention.

The fourth object of the invention is a kit for treating telangiectasias comprising a notice, a device for exsanguination of the blood vessels forming the invention for destroying the blood vessels forming the telangiectasias.

Advantageously,—the exsanguination device comprises a needle and/or an anaesthetic; and—the anaesthetic is in the form of a liquid to be injected or a cream to be applied to the skin.

BRIEF DESCRIPTION OF THE FIGURES

Other features, aims and advantages of the present invention will emerge from a reading of the following detailed description with regard to the figures given by way of non-limitative example and wherein.

DETAILED DESCRIPTION OF THE INVENTION

According to the present invention, the terms "from . . . to . . . " or "between . . . and . . . "used for defining ranges of values, must be understood as including the lower and upper bounds of these ranges.

Telangiectasias do not affect the health of patients but are considered not to be aesthetic. "Blood vessels forming the telangiectasias" means, within the meaning of the present invention, small veins, veinlets or arterioles, the diameter of which is less than or equal to approximately 0.3 mm. Beyond this diameter, it is no longer a case of blood vessels forming telangiectasias but reticular veins, in other words small varicose veins. The treatment of varicose veins does not fall within the scope of the invention.

The blood vessels forming the telangiectasias are situated in the dermis, at a depth of between 0.07 and 0.55 cm under the surface of the skin and, more particularly, at a depth of between 0.1 and 0.4 cm.

The invention relates to a device for destroying the blood vessels forming telangiectasias, avoiding destroying blood vessels that are in particular deeper or situated in the vicinity of telangiectasias and do not form telangiectasias. The device of the invention makes it possible to mechanically destroy only the blood vessels forming the telangiectasias. It comprises a cutting device, a device body, and a stop situated at a distance of between 0.1 cm and 0.6 cm from the distal end of said cutting device.

According to one embodiment, the cutting device comprises a single blade. The device with a single blade according to the invention makes it possible to be precise, and therefore to precisely and electively destroy the blood vessels forming the telangiectasias, which a multiblade device would not permit. The invention makes it possible to precisely follow the visible path followed by the vessels forming the telangiectasias.

In particular, the device of the invention intended to destroy the blood vessels forming the telangiectasias comprises a blade, a device body, and a stop situated at a distance of between 0.1 cm and 0.6 cm from the distal end of said blade, said one blade comprises a distal end, or distal part, and a proximal part. The distal part therefore corresponds to the end of the blade and is in the form of a point or rounded part, preferably in a point, for more precision. The proximal part of the blade is connected to the stop. The edges of the blade may, or may not, be sharp.

The blade may be made from any material known to persons skilled in the art, such as metal or ceramic. According to one embodiment, the blade is made from metal, and in particular the blade is made from stainless steel or carbon steel. According to another embodiment, the blade is made from ceramic. Preferably, the blade is made from ceramic, this material having better resistance than steel to repeated incisions.

The blade has a thickness of between 0.2 and 1 mm, in particular between 0.4 and 0.8 mm, preferably around 0.5 mm.

Figure 1:
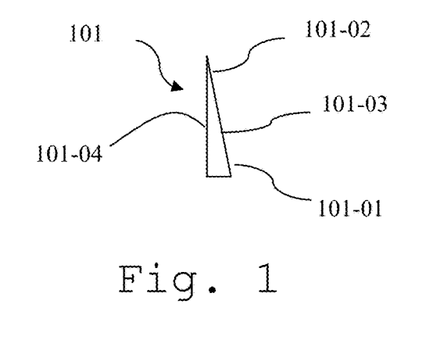
FIG. 1 is a schematic representation of a blade 101 according to an embodiment of the present invention, comprising a proximal part 101-01, a distal part 101-02, a sharp lateral edge 101-03 and a non-sharp or sharp lateral edge 101-04.

According to a preferred embodiment, the blade comprises a non-sharp lateral edge and a sharp lateral edge, the non-sharp lateral edge being substantially perpendicular to the blade-support part forming an angle of between 10° and 20° with the sharp lateral edge, preferably forming an angle of around 15° with the sharp lateral edge. The intersection between the sharp lateral edge and the non-sharp lateral edge forms the distal part of the blade, preferably in a point. Such an example of a blade is shown schematically in FIG. 1. The words "substantially perpendicular" mean, within the meaning of the present invention, an angle of between 88° and 92°, preferably an angle of 90°. The blade, in the proximal part thereof, has a width of between 0.2 and 1 cm, in particular between 0.3 and 0.8 cm, preferably around 0.5 cm.

According to another embodiment, the distal part is formed by the intersection of two sharp lateral edges forming between them an angle beta of between 10° and 90°, in particular between 15° and 45°, preferably around 20°. At the proximal part, the blade has a width of between 0.2 and 1 cm, in particular between 0.3 and 0.8 cm, preferably around 0.5 cm. Each of the two sharp lateral edges forms, with the blade-support part, respectively an angle gamma and an angle gamma' between 40° and 90°, the gamma and gamma' angles being identical or different, it being understood that the sum of the gamma, gamma' and beta angles is equal to 180°.

According to another embodiment, the distal part of the blade is formed by two sharp lateral edges, and is separated from the proximal part by two non-sharp lateral edges. The two sharp lateral edges form an angle delta of between 45° and 140° between them, in particular between 60° and 120°, preferably around 90°. The blade, in the proximal part thereof, has a width of between 0.2 and 1 cm, in particular between 0.3 and 0.8 cm, preferably around 0.5 cm. The two non-sharp lateral parts are substantially parallel and each of the two non-sharp lateral parts forms, with the blade-support part, a substantially perpendicular angle.

Figure 2:
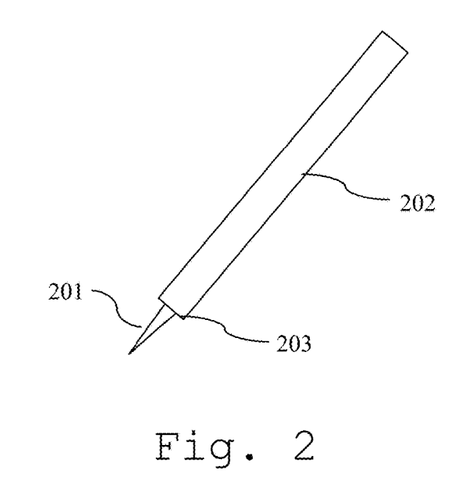
FIG. 2 depicts, according to an embodiment of the invention, a device for destroying the blood vessels forming the telangiectasias comprising a blade 201 and a device body comprising a gripping part 202 and a blade-support part 203 forming a stop.

One embodiment of the device of the invention comprising a blade is illustrated, for example, in FIG. 2.

According to one embodiment, the device comprises a blade and a broadened part supporting the blade, having a sufficient surface area, for example between 0.5 and 2 cm², for the skin of the body of the patient to offer sufficient resistance to the pressure exerted on the device when the telangiectasias are destroyed. Such an embodiment can, for example, be illustrated by FIG. 3.

The device body of the device of the invention comprises a gripping part and a blade support part.

The gripping part may be formed from any material known to persons skilled in the art. In particular the gripping part may be made from wood, metal or polymer. According to one embodiment, the gripping part is made from metal such as a steel, in particular a stainless steel, or a nickel alloy. According to another embodiment, the gripping part is made from polymer such as a plastics material or a rubber. In a preferred embodiment, the gripping part is made from polymer.

Figure 4:
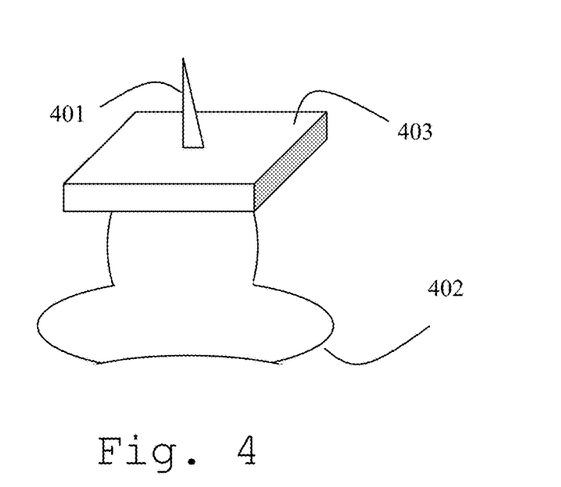
FIG. 4 depicts, according to another embodiment of the invention, a device for destroying the blood vessels forming the telangiectasias comprising a blade 401 and a device body comprising a gripping part 402 and a blade-support 403 coincident with the stop.

In one embodiment, the gripping part is in the form of a handle or a handpiece. According to a particular embodiment, the device of the invention comprises a blade and the gripping part is a handpiece (FIG. 4).

The blade-support part can be formed from any material known to persons skilled in the art. In particular, the blade-support part may be made from wood, metal or polymer. According to one embodiment, the blade support part is made from metal such as a steel, in particular a stainless steel, or a nickel alloy. According to another embodiment, the blade-support part is made from polymer such as a plastics material or a rubber. In a preferred embodiment, the blade-support part is made from polymer.

The gripping part and the blade-support part may be formed from the same material or from two different materials. According to one embodiment, the gripping part and the blade-support part are formed from the same material, and in particular the gripping part and the blade-support part are made from polymer. This preferred material makes it possible to reduce the cost of manufacturing an instrument, in principle for single use. The device body may be solid or hollow. According to one embodiment, the device body is hollow. It thus makes it possible to accommodate said one blade, when the latter is retractable.

The device of the invention further comprises a stop situated at a distance of between 0.1 cm and 0.6 cm from the distal end of said blade. Beyond 0.6 cm, the blade passes through the dermis. Below 0.1 cm, the blade is not deep enough to effectively cut the blood vessels forming the telangiectasias. In a particular embodiment, the stop is situated at a distance of between 0.2 cm and 0.4 cm from the distal end of said blade. Preferably, the stop is situated at a distance of around 0.3 cm from the distal end of said blade.

The stop has a sufficient surface area to limit the penetration of the blade, in the thickness of the skin, to a depth of less than 0.6 cm, when a pressure is applied to the skin by the application of the device.

The stop may be made from metal, polymer or ceramic. According to one embodiment, the stop is made from metal such as a carbon steel, a stainless steel or a nickel alloy. According to another embodiment, the stop is made from polymer such as a plastics material or a rubber. According to another embodiment, the stop is made from ceramic. According to a preferred embodiment, the stop is made from polymer. This preferred material makes it possible to reduce the cost of manufacturing an instrument, in principle for single use.

The stop may be moulded or not with one or other of the parts of the device of the invention. In particular, the stop may be moulded with the blade-support part, or the stop may be moulded with the blade.

The stop may be in various forms. For example, the stop may form a collar around said blade, or form a protuberance at at least one lateral edge, sharp or non-sharp, of said blade.

Figure 3:
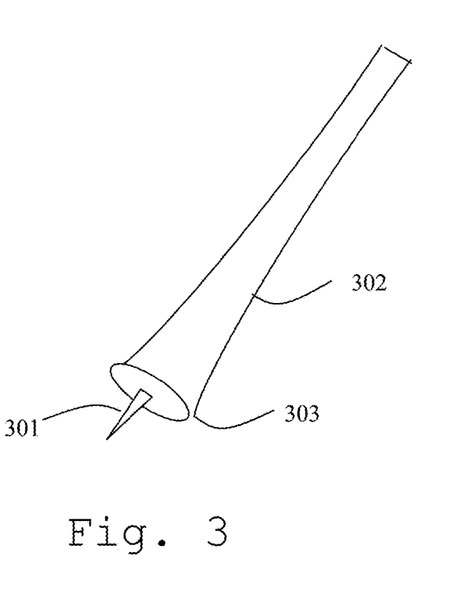
FIG. 3 depicts, according to another embodiment of the invention, a device for destroying the blood vessels forming the telangiectasias comprising a blade 301 and a device body comprising a gripping part 302 and a blade-support part 303 coincident with the stop.

The stop, connected to the proximal part of said blade, may be coincident with the blade support or be situated at a distance from the blade support. According to a preferred embodiment, the stop is coincident with the blade support. According to a particular embodiment, the stop is coincident with the blade-support part and forms a protuberance at at least one lateral edge, sharp or non-sharp, of said blade. An example of such an embodiment of the stop is illustrated in FIG. 3. According to another particular embodiment, the stop is coincident with the blade-support part and forms a protuberance at at least one lateral edge, sharp or non-sharp, of the blade. According to another particular embodiment, the stop is coincident with the blade-support part and forms a collar around said blade. According to another particular embodiment, the stop is coincident with the blade-support part and forms a collar around the blade.

According to a particular embodiment, the stop is not coincident with the blade-support part. In particular, the stop may be situated at a distance greater than 0.6 cm from the blade-support part when the device of the invention is not being used. When the device of the invention is being used, the stop comes to be placed in contact with the blade-support part, at a distance of between 0.1 and 0.6 cm from the distal end of said blade. According to another embodiment, the stop is situated at a distance from the blade-support part, in particular at a distance of between 0.05 and 1 cm from the blade support part, more particularly at a distance of between 0.1 and 0.6 cm from the blade-support part, preferably at a distance of between 0.2 and 0.4 cm from the blade-support part.

According to one embodiment, the device of the invention further comprises a needle. This needle may be fixed or retractable.

According to one embodiment, the device body is hollow and further comprises an inlet for an infiltration liquid.

Figures 5A, 5B:
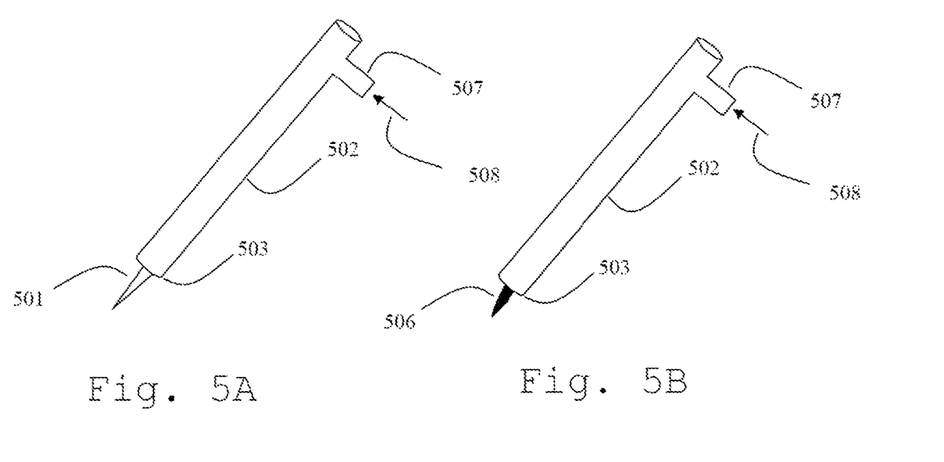
FIG. 5A depicts, according to another embodiment of the invention, a device for destroying the blood vessels forming the telangiectasias comprising a blade 501, a retractable needle 506, a device body comprising a gripping part 502, a blade-support part 503 coincident with the stop, and an inlet 507 for the infiltration liquid, the arrow 508 indicating the direction of flow of the infiltration liquid at the inlet of the device.
FIG. 5B depicts, according to another embodiment of the invention, a device for destroying the blood vessels forming the telangiectasias comprising a retractable needle 506, a device body comprising a gripping part 502, a blade-support part 503 coincident with the stop, and an inlet 507 for the infiltration liquid, the arrow 508 indicating the direction of flow of the infiltration liquid at the inlet of the device.

According to a particular embodiment, the device body is hollow and comprises an inlet for an infiltration liquid and said blade is retractable into said device body. According to an even more particular embodiment, an example of which is illustrated in FIG. 5, the device body is hollow, said blade is retractable into said device body, and the device of the invention further comprises a needle retractable inside the device body, so that, when said needle is inside the device body, then said blade is outside said device body, and vice versa. Within the meaning of the present invention, "is outside said device body" means a part projecting from the surface of said device body.

Figure 6A:
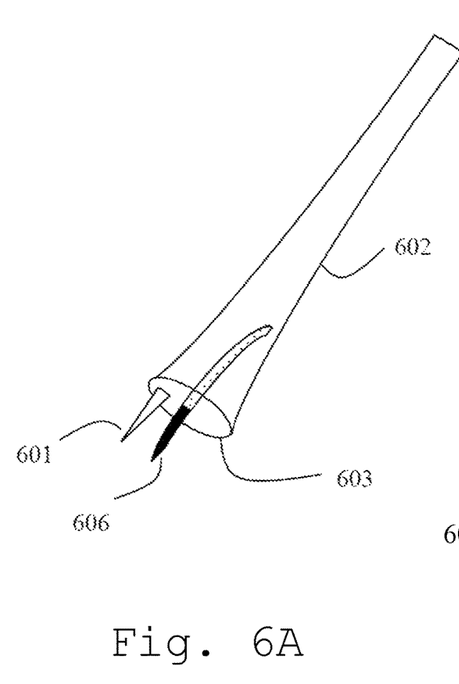
FIG. 6A shows schematically, according to another embodiment of the invention, a device for destroying the blood vessels forming the telangiectasias comprising a blade 601, a needle 606, and a device body comprising a gripping part 602 and a blade-support part 603 coincident with the stop; the needle part depicted in broken lines is situated inside the device body.
Figure 6B:
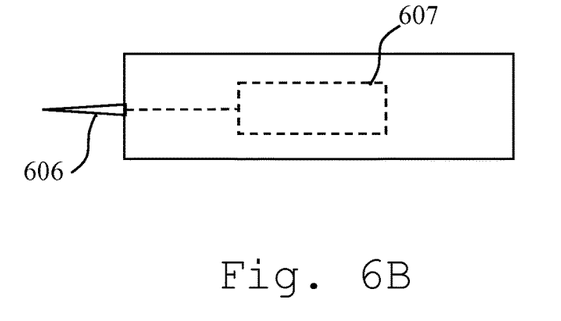
FIG. 6B shows schematically, according to another embodiment of the invention, a device for destroying the blood vessels forming the telangiectasias comprising a needle 606 and a device body, wherein a cartridge or carpule 607 is shown schematically placed within the device body and schematically connected to the needle 606.
Figure 7A:
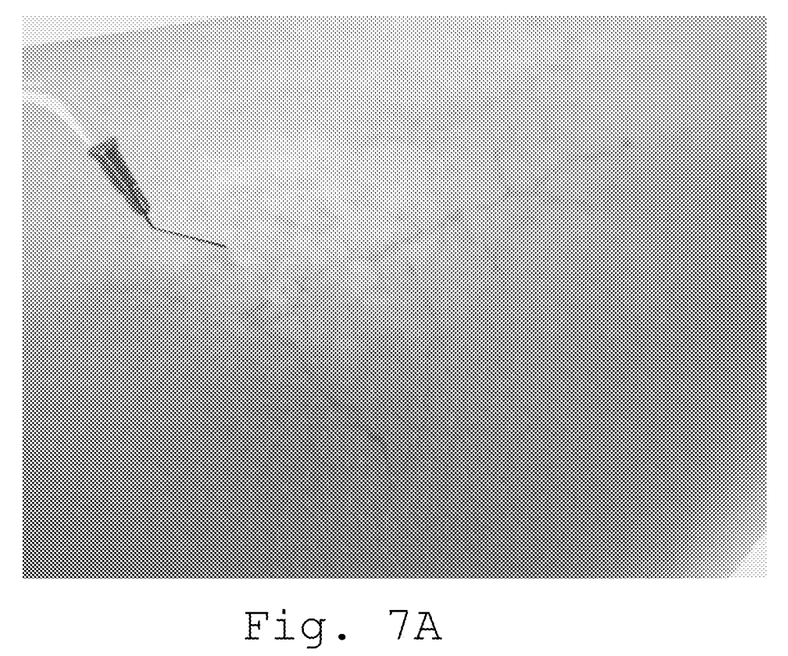
FIG. 7A shows schematically the exsanguination step, according to one embodiment of the method of the invention, in plan view.
Figure 7B:
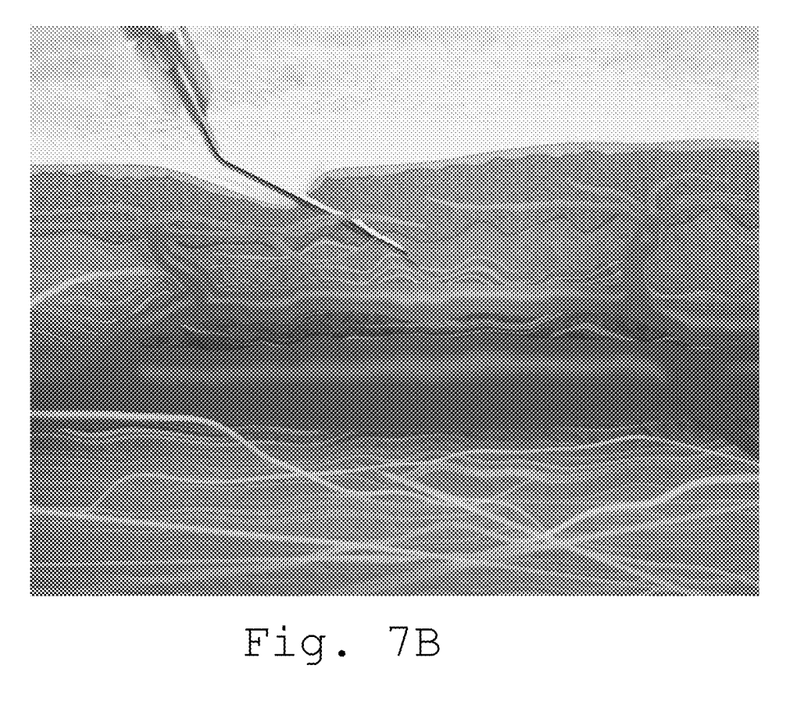
FIG. 7B shows schematically the exsanguination step, according to one embodiment of the method of the invention, in cross-sectional view.
Figure 8A:
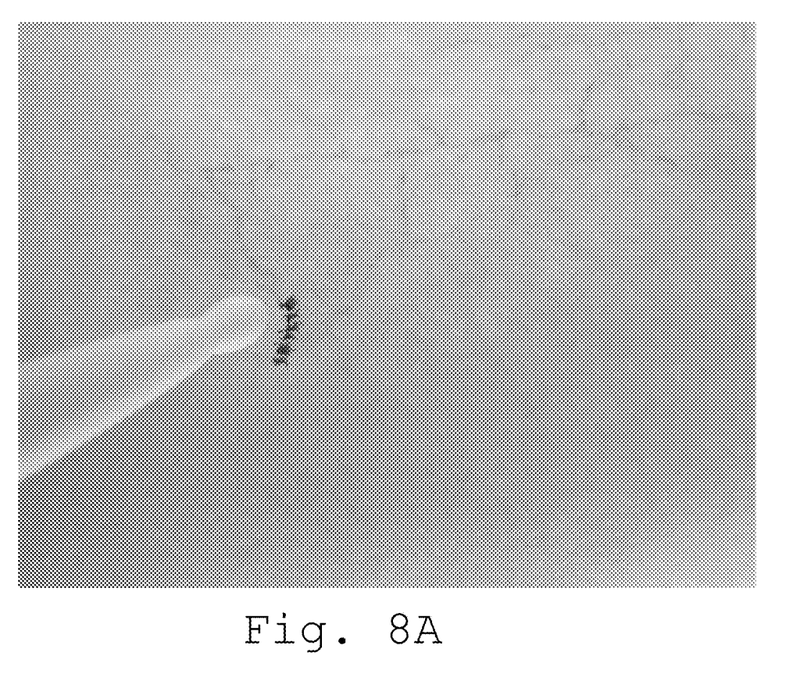
FIG. 8A shows schematically the step of destroying the blood vessels forming the telangiectasias, according to one embodiment of the method of the invention, in plan view.
Figure 8B:
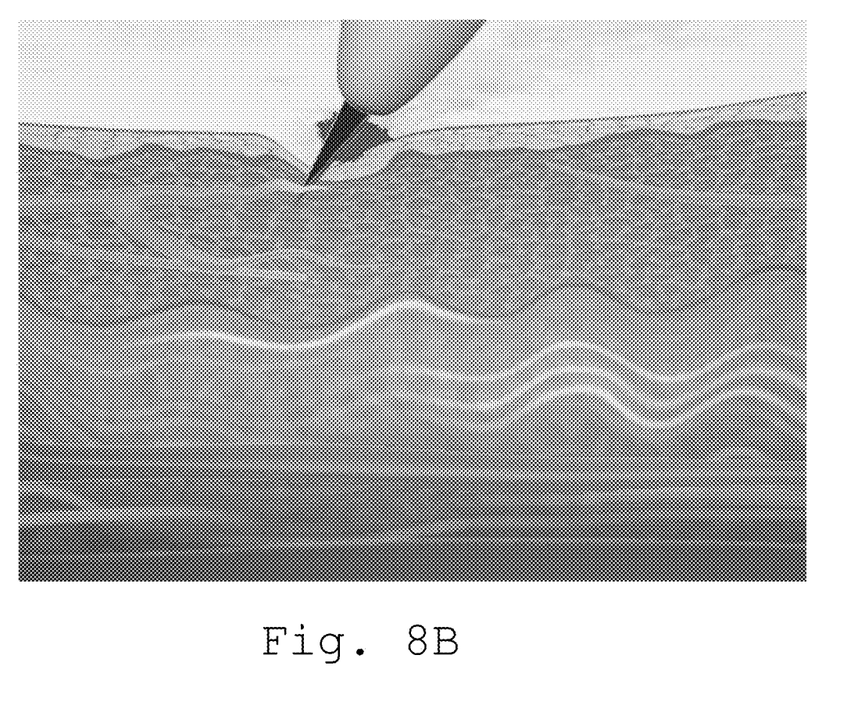
FIG. 8B shows schematically the step of destroying the blood vessels forming the telangiectasias, according to one embodiment of the method of the invention, in cross-sectional view.

According to another particular embodiment, the device body is hollow, comprises an inlet for an infiltration liquid and further comprises a fixed needle, projecting on the blade-support part. FIG. 6A illustrates an example of this particular embodiment. Even more particularly, FIG. 6B illustrates an embodiment wherein the needle is connected, inside the device body, to a cartridge, or carpule, containing an anaesthetic. This cartridge, or carpule, is illustrated schematically in interrupted lines in FIG. 6B as cartridge or carpule 607 placed within the device body and connected to the needle 606.

In all the embodiments of the invention, the distance between the stop and the distal end of said blade defines the depth of penetration of said blade. The stop thus enables said blade not to penetrate too deeply into the skin.

When the device of the invention also comprises a needle, it allows the implementation of the method of the invention, see below, by means of a single instrument, thus facilitating the use of the method.

The invention also relates to a method for the aesthetic treatment of telangiectasias. This method comprises local anaesthesia, exsanguination of the blood vessels forming the telangiectasias and mechanical destruction of the blood vessels forming the telangiectasias.

The local anaesthesia is achieved by any means known to persons skilled in the art. In particular, the local anaesthesia may result from the injection of an anaesthetic liquid or the application of an anaesthetic cream. Non-limitative examples of anaesthetic liquids are: lidocaine or isotonic bicarbonate, alone or in combination. Non-limitative examples of anaesthetic creams are: lidocaine or prilocaine, alone or in combination.

Exsanguination comprises the injection of a liquid that prevents recanalisation of the blood vessels because of the pressure exerted by the liquid. It should be noted, however, that, during exsanguination, the blood vessels are not completely emptied of the blood that they contain in order to avoid their no longer being visible. This is because it is necessary to be able to view the blood vessel during the following step of mechanical destruction.

According to one embodiment, the liquid injected during the exsanguination is an anaesthetic affording simultaneously local anaesthesia and exsanguination of the blood vessels forming the telangiectasias, by infiltration.

According to another embodiment, the liquid injected during exsanguination is water and the local anaesthesia is previously implemented, for example, by the topical application of an anaesthetic cream.

The blood vessels forming the telangiectasias are next destroyed by means of the device of the invention. This device being described above, the information relating thereto also applies in the context of the aesthetic treatment method.

The destruction of the blood vessels is implemented over the entire length of the blood vessel. In particular the mechanical destruction of the blood vessels forming the telangiectasias is implemented over the entire length of the blood vessels, by incisions preferably spaced apart by 0.1 to 0.5 cm.

The method for the aesthetic treatment of telangiectasias does not present any risk to the health of the patient since it is a case of solely surface treatment, at the epidermis and the dermis. Thus, if the blade cuts the skin at a point where there are no blood vessels forming telangiectasias, this does not give rise to any consequence since the cut is not deep. Only a risk of infection remains, common to all breakage of the epidermis, such as for example the secondary effects of a piercing or of a microabrasion of the skin.

The invention also relates to the device of the invention as described above for implementing the method of the invention defined above.

The invention also relates to the use of the device of the invention as described above during the implementation of the method of the invention defined above.

The invention also relates to a kit for the treatment of telangiectasias, comprising a notice, a device for exsanguination of the blood vessels forming the telangiectasias, and the device of the invention for destroying the blood vessels forming the telangiectasias. The exsanguination device comprises a needle and/or an anaesthetic. According to one embodiment, the exsanguination device comprises a needle. According to another embodiment, the exsanguination device comprises an anaesthetic. According to a particular embodiment, the exsanguination device comprises a needle and an anaesthetic.

According to a particular embodiment, the anaesthetic is present in the kit in the form of a liquid to be injected or a cream for topical application. Non-limitative examples of anaesthetic liquids are: lidocaine or isotonic bicarbonate, alone or in combination. Non-limitative examples of creams for topical application, or anaesthetic creams, are: lidocaine or psilocaine, alone or in combination.

The device for destroying the blood vessels forming telangiectasias being described above, the information relating thereto also applies in the context of the kit. According to a particular embodiment, the exsanguination device and the device for destroying the blood vessels forming telangiectasias form a single device.

The invention is in no way limited to the embodiments described and illustrated, which have been given only by way of examples.

The invention claimed is:

1. A device for destroying the blood vessels forming telangiectasias, comprising:
   a single blade;
   a device body;
   a needle,
   wherein the body comprises a gripping part adapted for gripping the device and a supporting part supporting the blade,
   wherein the blade comprises two lateral edges and forms, at a distal end thereof, a point, at least one of the two lateral edges being sharp,
   wherein the device comprises a stop situated at a distance in a range of from 0.1 to 0.6 cm from the distal end of the blade, the stop being adapted to limit the penetration of the blade, in a thickness of a skin of a patient, to a depth of less than or equal to 0.6 cm,
   wherein the device body is hollow, the needle being connected to a cartridge or carpule housed inside the device body.

2. The device according to claim 1, wherein the stop is situated at a distance in a range of from 0.2 and 0.4 cm from the distal end of said blade.

3. The device according to claim 1, wherein the gripping part is in the form of a handpiece.

4. The device according to wherein the blade is retractable into the device body.

5. The device according to claim 4, wherein the needle is retractable into the device body, the blade being adapted to be housed inside the device body when the needle is outside the device body, and the needle being adapted to be housed inside the device body when the blade is outside the device body.

6. The device according to claim 1, wherein the blade comprises a non-sharp lateral edge and a sharp lateral edge, the non-sharp lateral edge being substantially perpendicular to the supportinf part and forming an in a range of from 10° to 20° with the sharp lateral edge.

7. The device according to claim 6, wherein the non-sharp lateral edge forms an angle of approximately 15° with the sharp lateral edge.

8. The device according to claim 1, wherein the device is configured to destroy dilated intradermic blood vessels forming the telangiectasias, wherein the dilated intradermic blood vessels have a diameter of less than or equal to approximately 0.3 mm; and are situated at a depth in a range of from 0.1 to 0.4 cm under a surface of a skin of a patient.

9. A method for the aesthetic treatment of telangiectasias, comprising:
performing local anaesthesia in a zone of a body of a patient that has telangiectasias;
carrying out exsanguination of the dilated intradermal blood vessels forming the telangasias, wherein the dilated intradermal blood vessels forming the telangiectasias have a diameter of less than or equal to approximately 0.3 mm; and are situated at a depth in a range of from 0.1 to 0.4 cm under a surface of a skin of the patient;
providing a device comprising: a single blade; and a device body, wherein the body comprises a gripping part for gripping the device and a support part supporting the blade; wherein the blade comprises two lateral edges and forms, at a distal end thereof, a point, at least one of the two lateral edges being sharp, and wherein the device comprises a stop situated at a distance in a range of from 0.1 to 0.6 cm from the distal end of the blade limiting the penetration of the blade, in a thickness of the skin of the patient, to a depth of less than or equal to 0.6 cm; and
destroying the dilated intradermal blood vessels forming the telangiectasias mechanically using the device.

10. The method according to claim 9, wherein the local anaesthesia and the exsanguination of the blood vessels forming telangiectasias are implemented simultaneously by an infiltration.

11. The method according to claim 10, wherein the infiltration is by the injection of an anaesthetic.

12. The method according to claim 9, wherein the local anaesthesia is implemented by the application of an anaesthetising cream.

13. The method according to claim 9, wherein the exsanguination is implemented by an injection of liquid.

14. The method according to claim 9, wherein the mechanical destruction of the blood vessels forming telangiectasias is implemented over a length of the blood vessels, by incisions of the blood vessels.

15. The method according to claim 14, wherein the incisions of the blood vessels are spaced apart by 0.1 to 0.5 cm.

16. The method according to claim 9, wherein the local anaesthesia and the exsanguination of the blood vessels forming telangiectasias are implemented simultaneously by an infiltration using the device.

17. A kit for the treatment of telangiectasias comprising:
a notice,
a device for exsanguination of the blood vessels forming the telangiectasias, and
the device for destroying the blood vessels forming the telangiectasias according to claim 1.

18. The kit according to claim 17, wherein the exsanguination device comprises a needle and/or an anaesthetic.

19. The kit according to claim 18, wherein the anaesthetic is a liquid to be injected or a cream to be applied to the skin.

20. A method for the aesthetic treatment of telangiectasias, comprising:
providing the device according to claim 1;
performing local anaesthesia in a zone of a body of a patient that has telangiectasias using the device;
carrying out exsanguination of dilated intradermal blood vessels forming the telangiectasias, wherein the dilated intradermal blood vessels forming the telangiectasias have a diameter of less than or equal to approximately 0.3 mm; and are situated at a depth in a range of from 0.1 to 0.4 cm under a surface of a skin of the patient using the device; and
destroying the dilated blood vessels forming the telangiectasias mechanically using the device.

* * * * *